(12) United States Patent
Vardi

(10) Patent No.: US 11,096,701 B2
(45) Date of Patent: Aug. 24, 2021

(54) PERCUTANEOUS THROMBUS EXTRACTION DEVICE AND METHOD

(71) Applicant: Gil Vardi, St. Louis, MO (US)

(72) Inventor: Gil Vardi, St. Louis, MO (US)

(*) Notice: Subject to any disclaimer, the term of this patent is extended or adjusted under 35 U.S.C. 154(b) by 198 days.

(21) Appl. No.: 16/055,385

(22) Filed: Aug. 6, 2018

(65) Prior Publication Data

US 2018/0338771 A1 Nov. 29, 2018

Related U.S. Application Data

(62) Division of application No. 14/243,217, filed on Apr. 2, 2014, now Pat. No. 10,039,560, and a division of application No. 12/950,771, filed on Nov. 19, 2010, now Pat. No. 8,801,736.

(51) Int. Cl.
*A61B 17/22* (2006.01)
*A61B 17/221* (2006.01)

(52) U.S. Cl.
CPC ........... *A61B 17/22* (2013.01); *A61B 17/221* (2013.01); *A61B 2017/2215* (2013.01); *A61B 2017/22051* (2013.01); *A61B 2017/22054* (2013.01); *A61B 2017/22079* (2013.01); *A61B 2017/22094* (2013.01)

(58) Field of Classification Search
CPC .......... A61B 17/22; A61B 17/221; A61B 2017/22051; A61B 2017/22054; A61B 2017/22094; A61B 2017/22079; A61B 2017/2215; A61M 25/105; A61M 25/0108
See application file for complete search history.

(56) References Cited

U.S. PATENT DOCUMENTS

| | | |
|---|---|---|
| 4,614,188 A | 9/1986 | Bazell et al. |
| 4,650,466 A | 3/1987 | Luther |
| 5,011,488 A | 4/1991 | Ginsburg |
| 5,102,415 A * | 4/1992 | Guenther ............... A61B 17/22 604/103.05 |
| 5,868,708 A | 2/1999 | Hart et al. |
| 5,882,329 A | 3/1999 | Patterson et al. |

(Continued)

FOREIGN PATENT DOCUMENTS

WO WO2010023671 3/2010

OTHER PUBLICATIONS

International Search Report and Written Opinion for International Application No. PCT/US11/61377, dated Mar. 7, 2012, 14 pages.

*Primary Examiner* — Tuan V Nguyen
(74) *Attorney, Agent, or Firm* — David H. Cherwitz

(57) ABSTRACT

A percutaneous thrombus extraction device for removing a thrombus from within a blood vessel includes a flexible outer sheath defining a first passage between a proximal end and a distal end. An inner sheath is movably positionable within the first passage. The inner sheath defines a second passage between a proximal end and a distal end. The inner sheath is moveable in a radial direction between a collapsed configuration and an expanded configuration along a length of the inner sheath defined between the proximal end and the distal end. A catheter is movably positionable within the second passage, and has an expandable body at a distal end portion of the catheter. The expandable body is movable between a collapsed configuration and an expanded configuration.

20 Claims, 14 Drawing Sheets

(56) References Cited

U.S. PATENT DOCUMENTS

| | | |
|---|---|---|
| 5,902,263 A | 5/1999 | Patterson et al. |
| 5,941,869 A | 8/1999 | Patterson et al. |
| 5,947,985 A | 9/1999 | Imran |
| 5,971,938 A | 10/1999 | Hart et al. |
| 6,022,336 A | 2/2000 | Zadno-Azizi et al. |
| 6,319,242 B1 | 11/2001 | Patterson et al. |
| 6,544,276 B1 | 4/2003 | Azizi |
| 6,626,861 B1 | 9/2003 | Hart et al. |
| 6,685,722 B1 | 2/2004 | Rosenbluth et al. |
| 6,730,104 B1 | 5/2004 | Sepetka et al. |
| 6,824,545 B2 | 11/2004 | Sepetka et al. |
| 6,929,633 B2 | 8/2005 | Evans et al. |
| 6,994,718 B2 | 2/2006 | Groothuis et al. |
| 7,524,319 B2 | 4/2009 | Dubrul |
| 7,691,121 B2 | 4/2010 | Rosenbluth et al. |
| 7,691,123 B2 | 4/2010 | Tsugita et al. |
| 7,713,193 B2 | 5/2010 | Nance et al. |
| 7,763,010 B2 | 7/2010 | Evans et al. |
| 7,766,921 B2 | 8/2010 | Sepetka et al. |
| 7,799,046 B2 | 9/2010 | White et al. |
| 7,998,163 B2 | 8/2011 | Salahieh |
| 2001/0051810 A1 * | 12/2001 | Dubrul ................ A61B 17/221 606/159 |
| 2003/0212384 A1 | 11/2003 | Hayden |
| 2005/0143689 A1 | 6/2005 | Ramsey, III |
| 2005/0165366 A1 | 7/2005 | Brustad et al. |
| 2005/0261759 A1 | 11/2005 | Lambrecht et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2007/0010844 A1 | 1/2007 | Gong et al. |
| 2009/0182370 A1 * | 7/2009 | Volobuyev ................ A61F 2/01 606/200 |
| 2009/0248059 A1 | 10/2009 | Morsi |
| 2009/0299393 A1 | 12/2009 | Martin et al. |
| 2010/0081990 A1 | 4/2010 | Swisher |
| 2010/0217276 A1 | 8/2010 | Garrison et al. |

\* cited by examiner

PERCUTANEOUS THROMBUS EXTRACTION DEVICE AND METHOD

CROSS REFERENCE TO RELATED APPLICATIONS

This application is a divisional of U.S. patent application Ser. No. 14/243,217 which was filed on Apr. 2, 2014, and is now U.S. Pat. No. 10,039,560, which was a divisional application of U.S. patent application Ser. No. 12/950,771, filed Nov. 19, 2010, and is now U.S. Pat. No. 8,801,736, which are incorporated herein by this reference.

BACKGROUND

The subject matter described herein relates generally to a device suitable for extracting emboli, such as thrombi, from within a blood vessel and, more particularly, to an extraction device configured for percutaneous vascular introduction to remove a clot or thrombotic material without surgical intervention.

Standard treatment for thrombo-embolic disease or blood clots (e.g., embolism to the superficial femoral artery ("SFA") or treatment of dialysis access thrombosis) includes utilizing a embolectomy catheter, such as a Fogarty catheter including an inflatable balloon near a distal tip of the catheter to facilitate removal of emboli and thrombi (e.g., a blood clot) from within a blood vessel.

In the case of SFA, the patient undergoes general anesthesia in the operating room, a surgical incision is made and the artery is cut open by the surgeon. The catheter is inserted and pushed across the embolism or thrombus, the balloon is inflated to match a diameter of the artery and pulled back until the thrombus and the balloon are pulled outside of the body through the incision. This procedure requires general anesthesia and a surgical approach. Thus, the procedure is risky to the patient and very costly, requiring a hospital stay.

BRIEF DESCRIPTION

In one aspect, a catheter that includes a body portion having a distal end and a proximal end. The body portion defines a passage between the distal end and the proximal end. A first expandable body is positioned at a distal end portion of the catheter that is movable between a collapsed configuration and an expanded configuration. A second expandable body is positioned at an opposing proximal end portion of the catheter. The passage provides fluid communication between the second expandable body and the first expandable body. The second expandable body is movable between a collapsed configuration and an expanded configuration.

In another aspect, an extraction device includes a flexible outer sheath defining a first passage between a proximal end and a distal end, and an inner sheath movably positionable within the first passage. The inner sheath defines a second passage between a proximal end and a distal end. The inner sheath is movable in a radial direction between a collapsed configuration and an expanded configuration along a length of the inner sheath defined between the proximal end and the distal end. The inner sheath is self-expandable to the expanded configuration to conform to an inner surface of the blood vessel.

In yet another aspect, a system includes a flexible outer sheath defining a first passage between a first proximal end and a first distal end, and an inner sheath movably positionable within the first passage. The inner sheath defines a second passage between a second proximal end and a second distal end. The inner sheath is movable in a radial direction between a collapsed configuration and an expanded configuration along a length of the inner sheath defined between the second proximal end and the second distal end. At least a portion of the inner sheath contacts an inner surface of the blood vessel when the inner sheath is extended from the first distal end and in the expanded configuration.

DETAILED DESCRIPTION

The embodiments described herein provide an extraction device that can be introduced into a blood vessel percutaneously for extracting emboli or thrombi from within the blood vessel. The minimally invasive percutaneous introduction reduces or minimizes trauma to the patient without the need for general anesthesia or hospitalization, which leads to improved patient comfort and safety, as well as major savings to the health care system. Although the embodiments have been described herein with relation to extracting emboli or thrombi from within a blood vessel in the patient's cardiovascular system, it should be apparent to those skilled in the art that the extraction device described herein may be suitable for other extraction procedures, such as removing stones from biliary tubes, for example.

Figure 1:
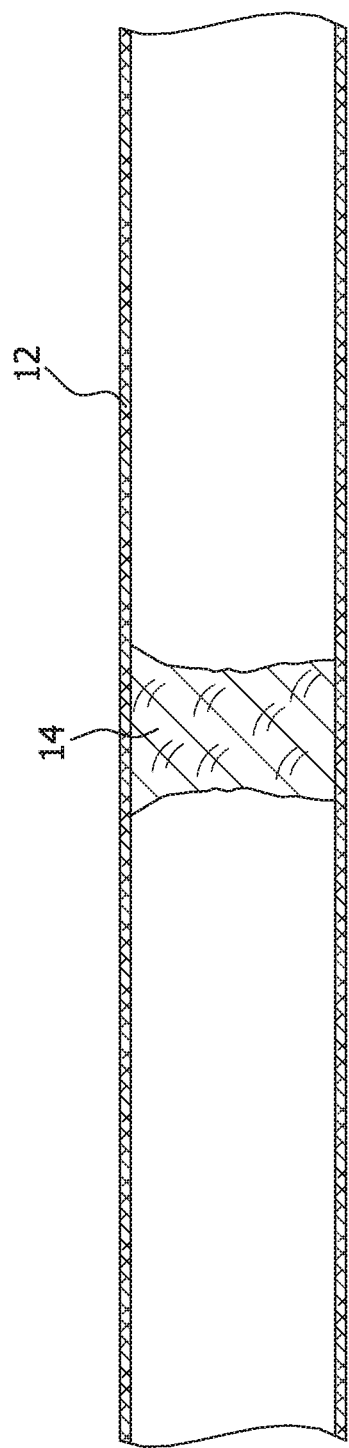
FIG. 1 is a schematic sectional view of a blood vessel with a thrombus occluding flow of blood through the blood vessel.
Figure 2:
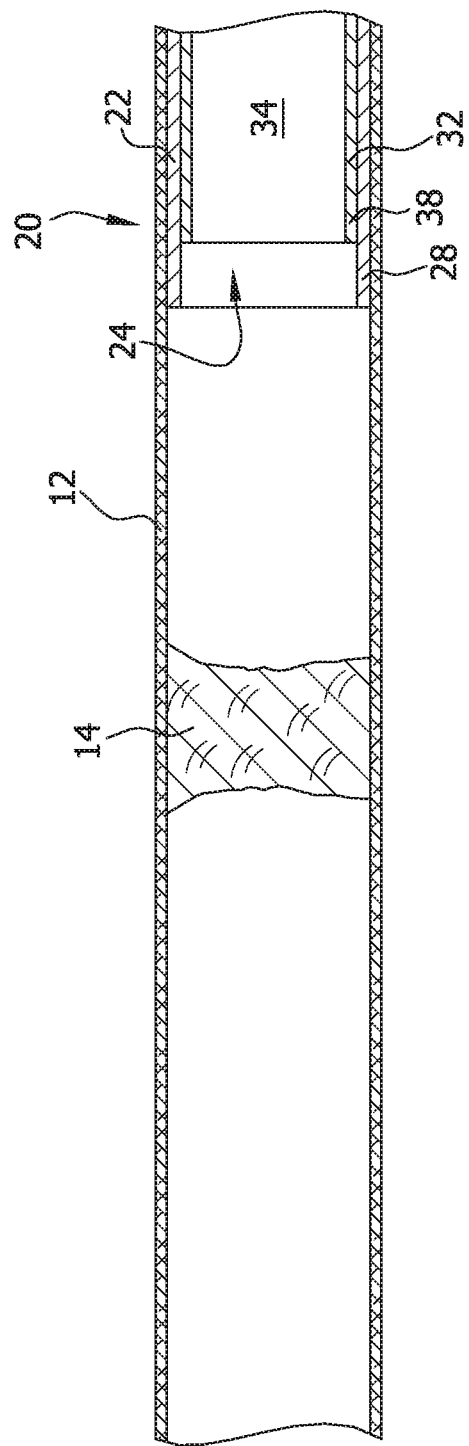
FIG. 2 is a schematic sectional view of an extraction device partially positioned within the blood vessel.

FIG. 1 is a schematic sectional view of a blood vessel 12 with a thrombus 14 occluding flow of blood through blood vessel 12. Referring to FIGS. 2-5, in one embodiment an extraction device 20 is configured for removing thrombus 14 from within blood vessel 12. Extraction device 20 includes a flexible outer tube or sheath 22 that defines a passage 24 between a proximal end (not shown) and an opposing distal end 28, as shown in FIG. 2. Outer sheath 22 is a flexible tube suitable for percutaneously introduction into a vessel, such as blood vessel 12, using techniques known to those skilled in the art. Outer sheath 22 is made of a suitable biocompatable material including, without limitation, an elastomer, such as silicone rubber, natural rubber, polyvinylchloride, polyurethane, polyester, polytetrafluoroethylene, and similar materials. In certain embodiments, outer sheath 22 is made of a composite material including an incorporated reinforcement material or structure to provide desired strength, flexibility, torqueability, and/or durability. The construction of catheter tubes suitable for percutaneous vascular introduction is well described in medical references.

A flexible inner tube or sheath 32 is movably positionable within passage 24 defined along a length of outer sheath 22. In a collapsed or partially collapsed configuration, inner sheath 32 is freely movable through passage 24 defined through outer sheath 22 to position inner sheath 32 proximate thrombus 14. Inner sheath 32 has a suitable outer diameter to facilitate reciprocal movement of inner sheath 32 within outer sheath 22. Inner sheath 32 defines a passage 34 between a proximal end (not shown) and an opposing distal end 38 of inner sheath 32. Inner sheath 32 is moveable or expandable in a radial direction between a collapsed configuration and an expanded configuration substantially along an entire length of inner sheath 32 defined between the proximal end and distal end 38. Unlike conventional expandable sheaths that expand only at a distal end portion, inner sheath 32 is expandable along substantially the entire length of inner sheath 32 such that an inner cross-sectional area of passage 34 increases along the length of inner sheath 32 as inner sheath 32 is expanded. Because the cross-sectional area of passage 34 increases along an entire length of inner sheath 32, relatively larger emboli, thrombi, and/or other occluding particles can be easily removed from within blood vessel 12 utilizing inner sheath 32, as described herein.

Suitable flexible materials for use in constructing inner sheath 32 may include, without limitation, the materials suitable for constructing outer sheath 22 as set forth above. In one embodiment, inner sheath 32 is self-expandable in a radial direction from an initial collapsed configuration, which facilitates movement or translation of inner sheath 32 through outer sheath 22, to the expanded configuration, wherein inner sheath 32 has a diameter corresponding to an inner diameter of blood vessel 12 that is larger than a diameter of inner sheath 32 in the collapsed configuration. In the expanded configuration, inner sheath 32 substantially conforms to the inner surface of blood vessel 12.

Figure 5:
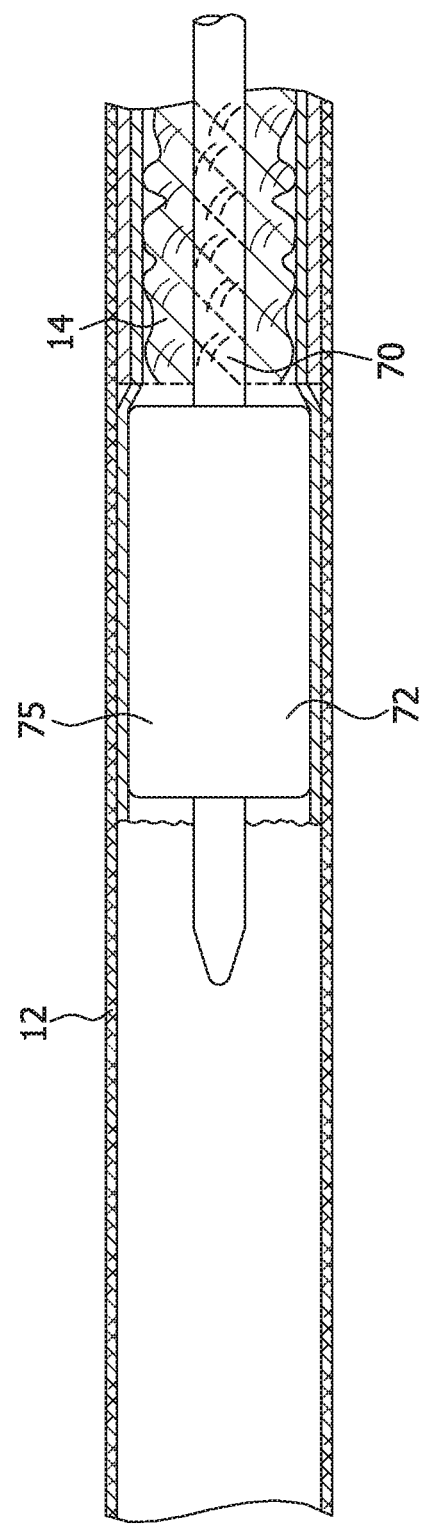
FIG. 5 is a schematic sectional view of the extraction device shown in FIG. 3 with an expandable body of the catheter retracted into a distal end portion of the inner sheath to facilitate removal of the thrombus from within the blood vessel.

In one embodiment, with inner sheath 32 positioned proximate thrombus 14, inner sheath 32 expands in a radial direction along a length of inner sheath 32 to contact the inner surface of blood vessel 12 as outer sheath 22 is extracted from within blood vessel 12. In one embodiment, outer sheath 22 is at least partially extracted from within blood vessel 12 to allow inner sheath 32 to expand in a radial direction along at least a portion of the length of inner sheath 32. In a particular embodiment, outer sheath 22 is completely extracted from within blood vessel 12 and removed through the incision to allow inner sheath 32 to expand in a radial direction along the entire length of inner sheath 32. As inner sheath 32 extends from distal end 28 of outer sheath 22, inner sheath 32 in the expanded configuration contacts the inner surface of blood vessel 12. In an expanded configuration, a distal end 40 of inner sheath 32 is configured to retain thrombus 14 to facilitate removal of thrombus 14 from within blood vessel 12, as shown in FIG. 5. In certain embodiments, the expansion of inner sheath 32 is reversible, i.e., inner sheath 32 is urged from the expanded configuration to a collapsed or partially collapsed configuration, to facilitate removal of inner sheath 32 from within blood vessel 12 to complete the procedure. By urging inner sheath 32 to a collapsed or partially collapsed configuration having a smaller diameter, potential injury or trauma to blood vessel 12 is reduced or minimized in contrast to conventional sheaths having a fixed larger diameter, which may cause the blood vessel to tear as the conventional sheath is inserted into and/or removed from within the blood vessel. In an alternative embodiment, only one sheath, for example inner sheath 32, is utilized. In this alternative embodiment, inner sheath 32 is self-expandable or expandable using any suitable mechanism, such as a crank or another structural mechanism of the sheath, rotation, heating, or a suitable balloon.

To provide for sufficient expansion of inner sheath 32, at least a portion of inner sheath 32 may be constructed of a suitably resilient material, such as a material having desired shape memory properties. For example, inner sheath 32 may be fabricated at least partially from suitable materials having shape memory properties including, without limitation, Nitinol and other known shape memory alloys (SMA) having properties that develop a shape memory effect (SME), which allows the material to return to an initial configuration after a force or heating process applied to the material to shape, stretch, compress and/or deform the material is removed. In a further embodiment, inner sheath 32 may be fabricated from a thermally treated metal alloy (TMA) including, without limitation, nickel titanium, beta titanium, copper nickel titanium, cobalt chrome, stainless steel, and any combination thereof. In an alternative embodiment, inner sheath 32 is expandable using a balloon and/or another mechanism suitable to facilitate expanding inner sheath 32. In a particular embodiment, inner sheath 32 is fabricated at least partially from a suitable polymeric material, such as a polyurethane material. It should be apparent to those skilled in the art that inner sheath 32 may be made or fabricated using any suitable biocompatible material preferably, but not necessarily, having suitable shape memory properties. Further, inner sheath 32 may be made or fabricated using any suitable polymer-coated alloy including, without limitation, a nickel titanium alloy coated with polytetrafluoroethylene (PTFE).

In particular embodiments, inner sheath 32 is made from a mesh material having an outer diameter of about 1 millimeter (mm) to about 30 mm and including one or more wires forming the mesh material. In one particular embodiment, inner sheath 32 includes a mesh material of 24-72 wires each having a diameter of about 10 microns to about 100 microns. The wires may comprise stainless steel, cobalt chrome, nickel titanium, polyester filaments (such as a polymeric expandable monofilament), and suitable combinations thereof. The wires may also be coated with PTFE or parylene, for example. In this embodiment, the braiding angle is about 120 degrees and a distance between wires is about 0.05 mm to about 0.5 mm.

Figure 3:
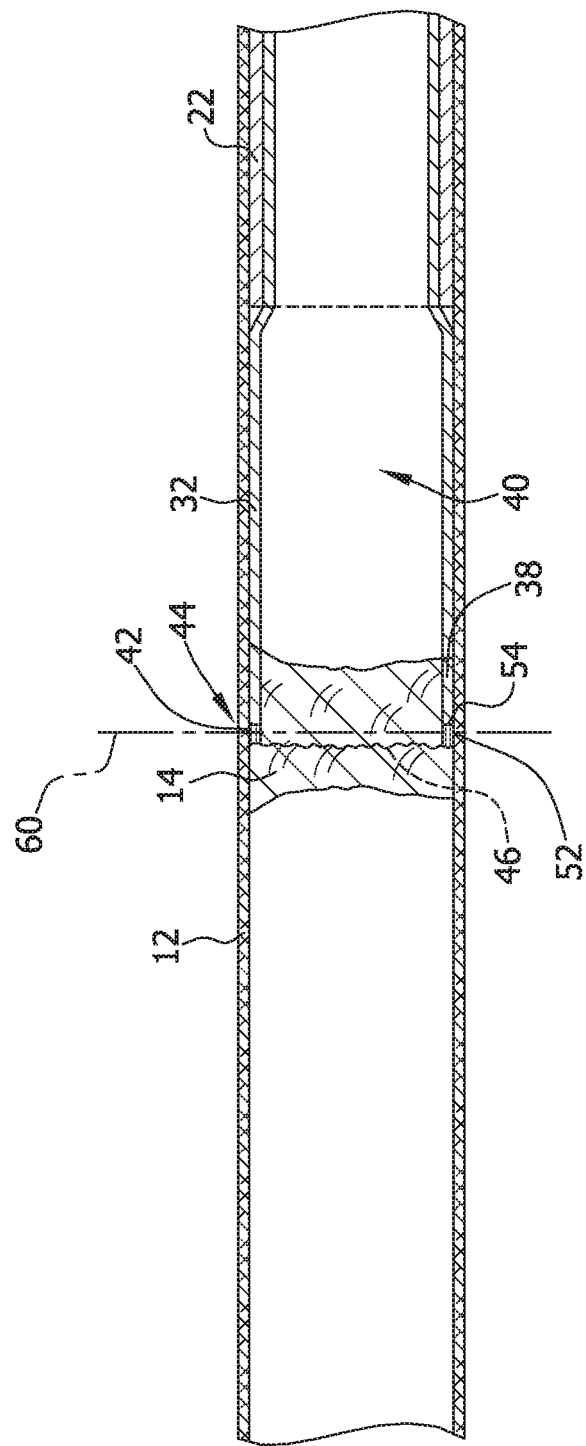
FIG. 3 is a schematic sectional view of the extraction device shown in FIG. 2 with an inner sheath partially extending from a distal end of an outer sheath and expanded to contact an inner surface of the blood vessel.

In the exemplary embodiment, extraction device 20 includes one or more radio opaque markers located on inner sheath 32 to indicate whether distal end 40 of inner sheath 32 is in a radially expanded configuration. In certain embodiments, two or more markers are positioned about a circumference of inner sheath 32. For example, two markers may be positioned about 180 degrees apart along the circumference of inner sheath 32. As shown, for example, in FIG. 3, extraction device 20 includes a first radio opaque marker 42 located at a first position 44 on a circumferential edge 46 of distal end 38 and a second radio opaque marker 52 located at a second position 54 on circumferential edge 46 of distal end 38 opposing first position 44 to facilitate determining whether distal end 40 of inner sheath 32 is in a radially expanded configuration or a convergent configuration, for example. When inner sheath 32 is collapsed, first radio opaque marker 42 is very close to second radio opaque marker 52, and when inner sheath 32 expands a distance between first radio opaque marker 42 and second radio opaque marker 52 increases to allow an operator using fluoroscopy to determine whether inner sheath 32 is in a collapsed configuration or an expanded configuration, for example. In an alternative embodiment, the radio opaque marker includes a string positioned about a circumference of inner sheath 32. The string is seen as a small circle when inner sheath 32 is collapsed and as a relatively larger circle when inner sheath 32 expands. As shown in FIG. 3, first position 44 and second position 54 are located on a line 60 defining a diameter of inner sheath 32 with inner sheath 32 in the radially expanded configuration.

Figure 4:
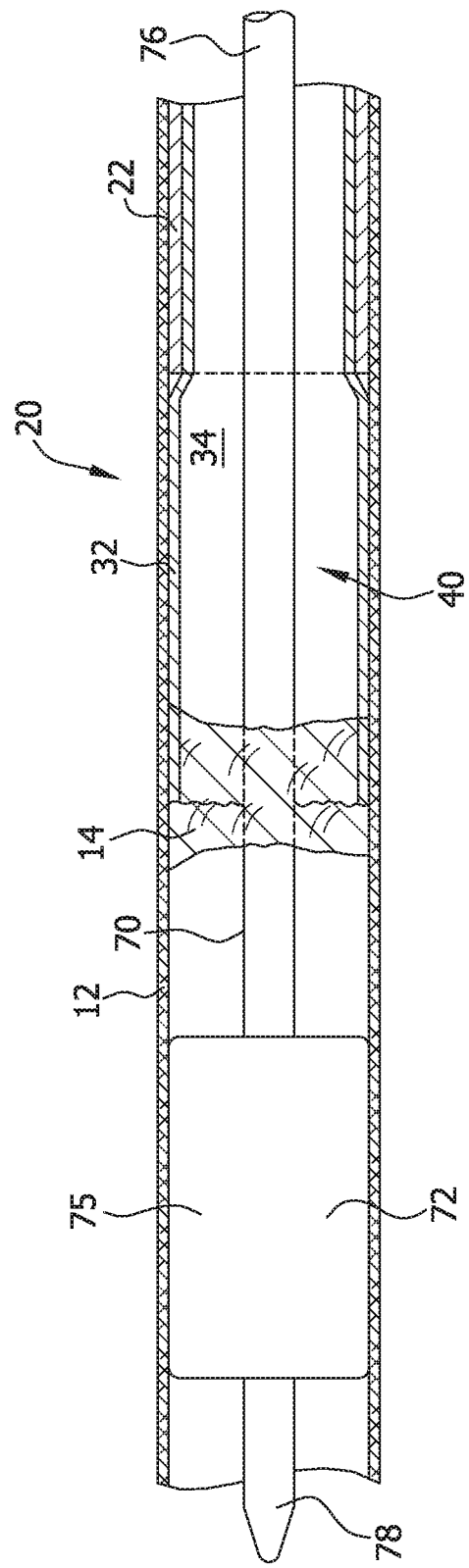
FIG. 4 is a schematic sectional view of the extraction device shown in FIG. 3 with a catheter introduced into the inner sheath and extending through the thrombus.

Referring further to FIGS. 4 and 5, in the exemplary embodiment extraction device 20 includes a suitable mechanism, such as a catheter 70, a tube, or a wire, movably positionable within passage 34 defined through inner sheath 32. In the exemplary embodiment, catheter 70 includes a body portion 74 that defines a passage 76 between a proximal end portion (not shown in FIGS. 4 and 5) and an opposing distal end portion 78 of catheter 70. A first expandable body 72 is positioned at distal end portion 78 of catheter 70. First expandable body 72 is movable between a radially collapsed configuration and a radially expanded configuration, as shown in FIGS. 4 and 5. In a particular embodiment, first expandable body 72 includes an inflatable balloon 75, as shown in FIGS. 4 and 5, that is inflatable to move from a collapsed or deflated configuration to an inflated configuration. In the inflated configuration, balloon 75 conforms to the inner surface of blood vessel 12 to facilitate removing thrombus 14 from within blood vessel 12 and transferring thrombus 14 into expanded inner sheath 32. Balloon 75 is constructed of a suitable material including, without limitation, polytetraflouroetylene and polyolefin materials, such as a polyethylene material. It should be apparent to those skilled in the art that balloon 75 may be made or fabricated using any suitable biocompatible material, the construction of which is well described in medical references.

Figure 6:
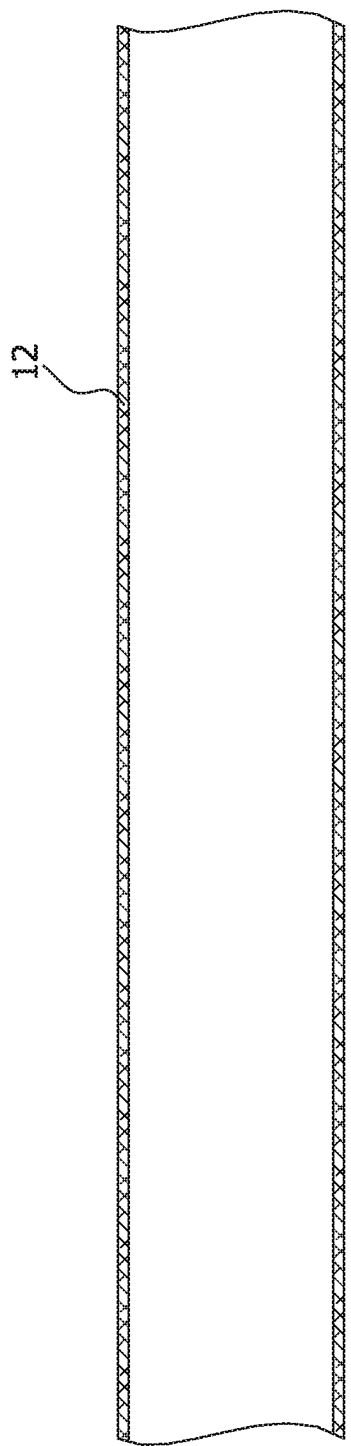
FIG. 6 is a schematic sectional view of the blood vessel shown in FIG. 1 with the thrombus removed from within the blood vessel.

In an alternative embodiment, first expandable body 72 includes one or more wire coils or one or more flexible members forming an umbrella-shaped or disc-shaped expandable body (none of which are shown) provided at distal end 78 of catheter 70 that are movable between a collapsed or retracted configuration and a radially expanded configuration. With first expandable body 72 in the expanded configuration, catheter 70 is translated in a proximal axial direction through blood vessel 12 to urge thrombus 14 into inner sheath 32 to facilitate removing thrombus 14 from within blood vessel 12. FIG. 6 is a schematic sectional view of blood vessel 12 shown in FIG. 1 with thrombus 14 removed from within blood vessel 12. In one embodiment, a vessel closure device (not shown) including, for example, a suture or a swelling material, may be operatively coupled to outer sheath 22 or inner sheath 32 so that with thrombus 14 removed from within blood vessel 12 the incision site in blood vessel 12 can be closed upon removal of outer sheath 22 and/or inner sheath 32.

Figure 7:
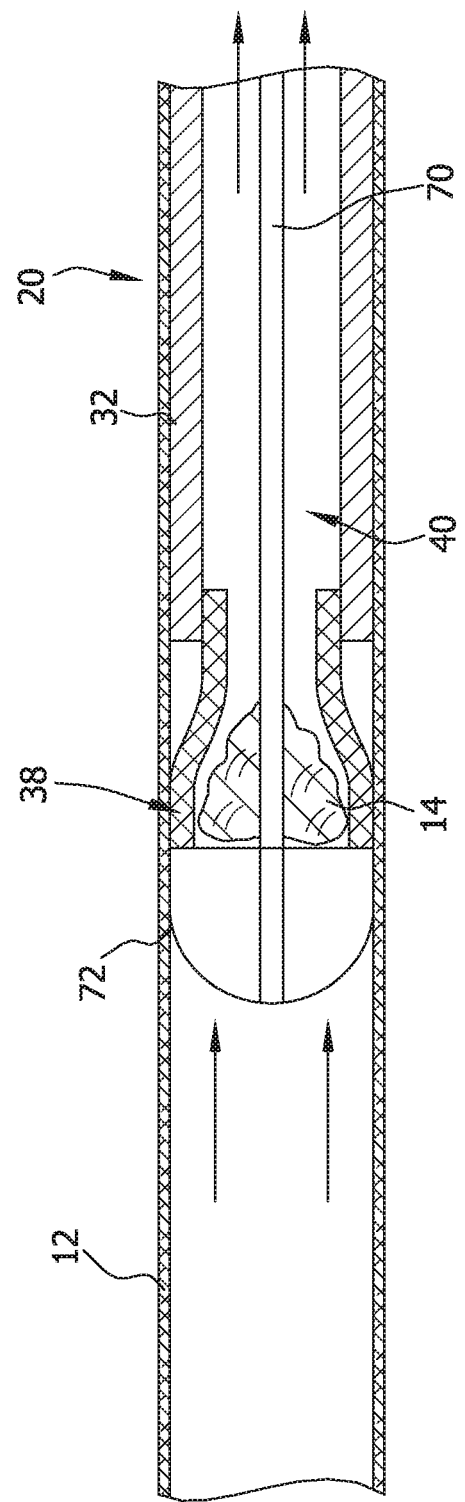
FIG. 7 is a schematic sectional view of an extraction device with an expandable body of the catheter sealing a distal end portion of the inner sheath to facilitate removal of the thrombus from within the blood vessel.
Figure 8:
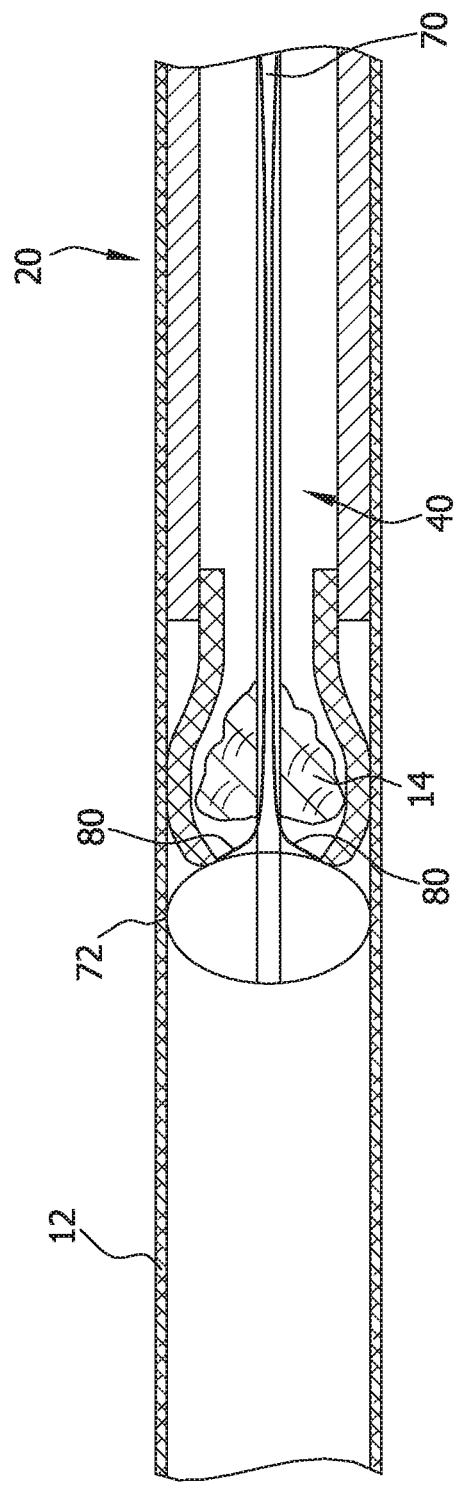
FIG. 8 is a schematic sectional view of an alternative extraction device with one or more compression strings configured to close a distal end portion of the inner sheath to facilitate removal of the thrombus from within the blood vessel.

In a particular embodiment, as shown in FIG. 7, at least a portion of inner sheath 32 is made of a suitable mesh material. With thrombus 14 positioned within distal end 38 of inner sheath 32, first expandable body 72 is positioned against inner sheath 32, such as by pulling catheter 70 in the proximal axial direction, to seal distal end 38 of inner sheath 32 to facilitate removal of thrombus 14 from within blood vessel 12. In one embodiment, a suitable negative pressure may be applied to maintain thrombus 14 positioned within inner sheath 32 to facilitate removing thrombus 14 from blood vessel 12 and/or to aspirate the dislodged thrombus 14 into inner sheath 32. Referring further to FIG. 8, one or more compression strings 80 may be positioned about and operatively coupled to circumferential edge 46 of distal end 38 to provide closure to distal end portion 40, as desired, to maintain thrombus 14 within inner sheath 32. With thrombus 14 positioned within inner sheath 32, compression string 80 is pulled to urge distal end portion 40 closed and seal distal end 38 of inner sheath 32 to facilitate removal of thrombus 14 from within blood vessel 12. In alternative embodiments, other suitable mechanisms including, without limitation, heat, one or more wires, and/or a balloon or another expandable body, may be utilized to seal distal end 38 of inner sheath 32 to secure thrombus 14 within inner sheath 32.

Figure 9:
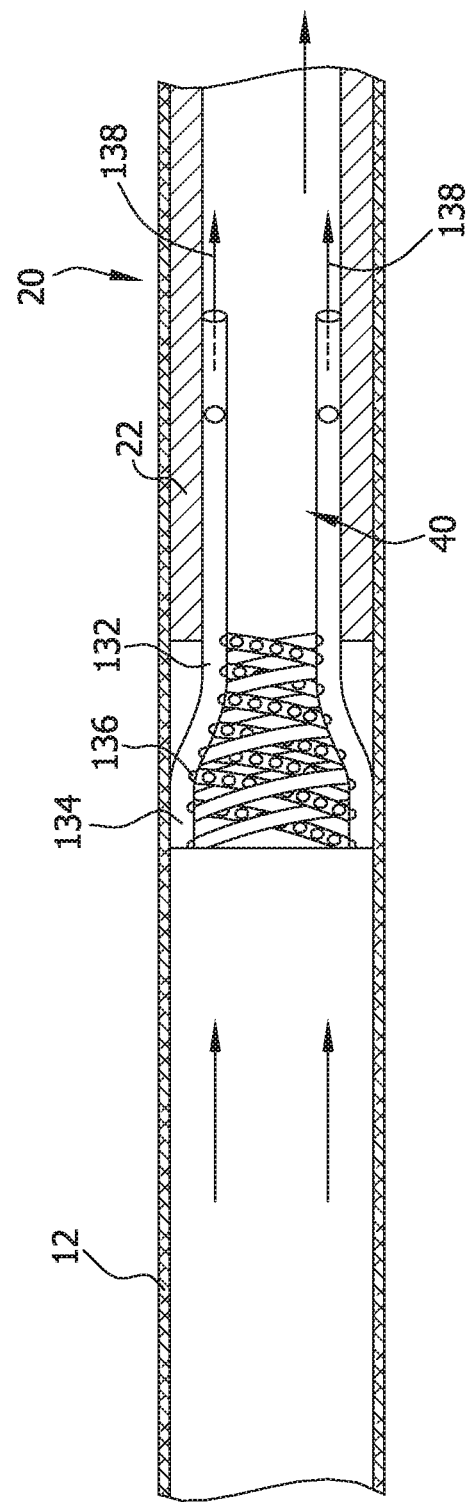
FIG. 9 is a schematic sectional view of an alternative extraction device with an inner sheath partially extending from a distal end of an outer sheath and expanded to contact an inner surface of the blood vessel.

FIG. 9 is a schematic sectional view of extraction device 20 with an inner sheath 132 partially extending from a distal end of outer sheath 22 and expanded to contact an inner surface of blood vessel 12. In a particular embodiment, as shown in FIG. 9, at least a portion of inner sheath 132 is made of a suitable mesh material including one or more tubes 134. A plurality of apertures 136 are defined through tubes 134 to provide fluid communication between an inner lumen of tube 132 and blood vessel 12. A suitable negative pressure, indicated by directional arrows 138, may be applied through apertures 136 to maintain thrombus 14 (not shown in FIG. 9) positioned within inner sheath 132 to facilitate removing thrombus 14 from blood vessel 12 and/or to aspirate the dislodged thrombus 14 into inner sheath 132.

Figure 10:
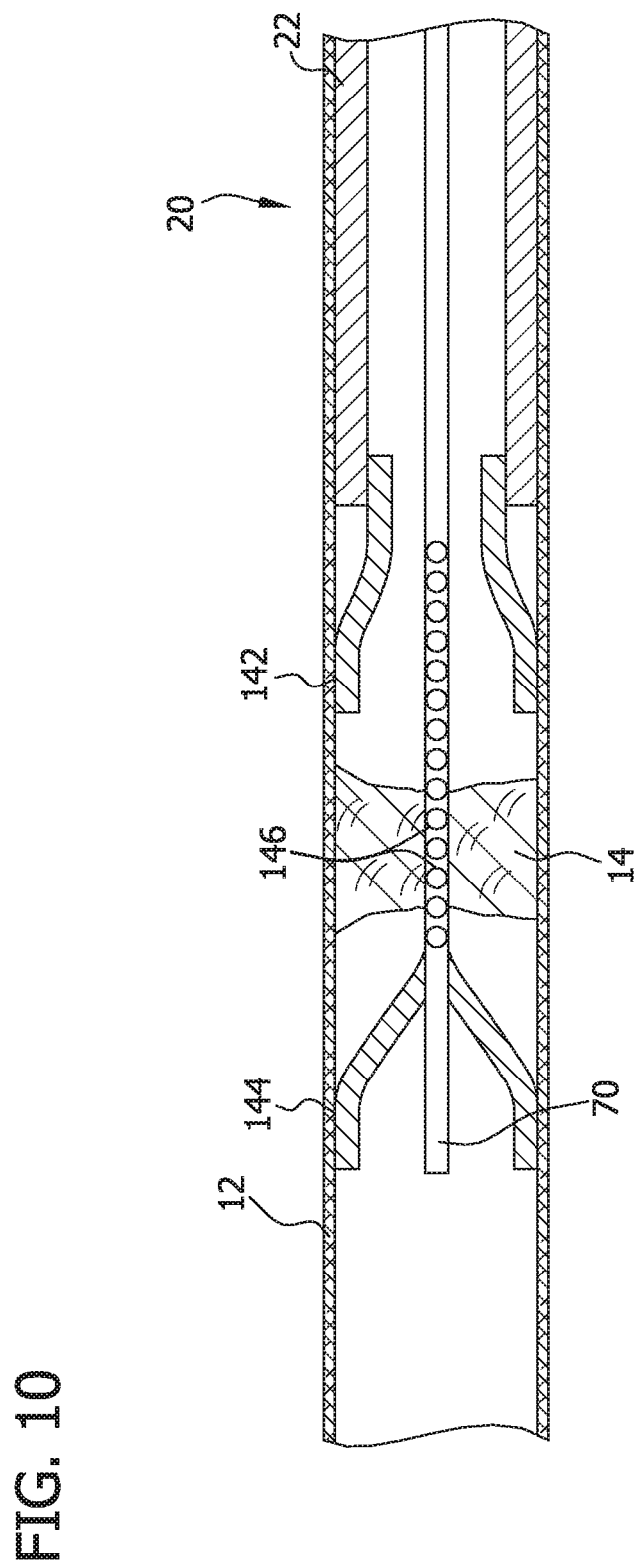
FIG. 10 is a schematic sectional view of an alternative extraction device with a catheter introduced into an inner sheath of the extraction device and extending through the thrombus.
Figure 11:
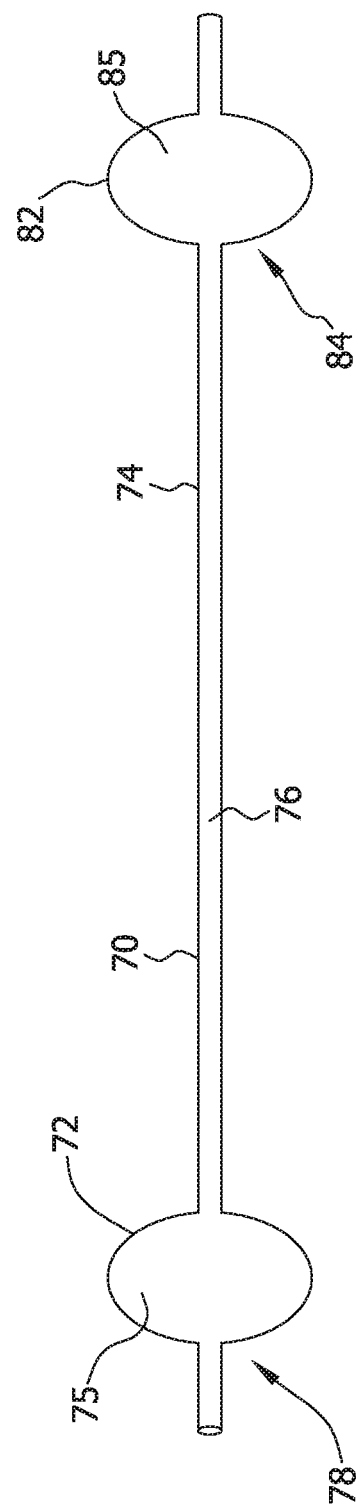
FIG. 11 is a schematic side view of an exemplary catheter suitable for use with the extraction device shown in FIGS. 2-5.

FIG. 10 is a schematic sectional view of extraction device 20 with catheter 70 introduced into an inner sheath 142 and extending through thrombus 14. In this embodiment, as shown in FIG. 10, a second inner sheath 144 is positioned distally to inner sheath 142. With catheter 70 extended through thrombus 14, second inner sheath 144 is expanded to contact an inner surface of blood vessel 12. In a particular embodiment, inner sheath 142 and/or second inner sheath 144 are made of a suitable mesh material. A plurality of apertures 146 are defined through catheter 70 to provide fluid communication between an inner lumen of catheter 70 and blood vessel 12. A suitable negative pressure may be applied through apertures 146 to draw thrombus 14 into inner sheath 142 to facilitate removing thrombus 14 from blood vessel 12 and/or to aspirate the dislodged thrombus 14 into inner sheath 142.

Referring now to FIGS. 11-14, in the exemplary embodiment, a second or external expandable body 82 is positioned at an opposing proximal end portion 84 of catheter 70 that extends outwardly from blood vessel 12 and percutaneously through the entry incision external to the patient's body. Passage 76 defined through body portion 74 provides fluid communication between second expandable body 82 and first expandable body 72. A suitable liquid or gas, such as carbon dioxide or air, can be transferred between first expandable body 72 and second expandable body 82 to expand or collapse expandable body 72, as desired. Second expandable body 82 is movable between a collapsed configuration and a radially expanded configuration. In the exemplary embodiment shown in FIGS. 11-14, second expandable body 82 includes an inflatable balloon 85 that is inflatable to move from a collapsed or deflated configuration to an inflated configuration. In the exemplary embodiment, second balloon 85 is similar in size and configuration to first balloon 75, although in alternative embodiments, second balloon 85 may have different dimensions and/or a different configuration than the dimensions and/or the configuration of first balloon 75.

Figure 12:
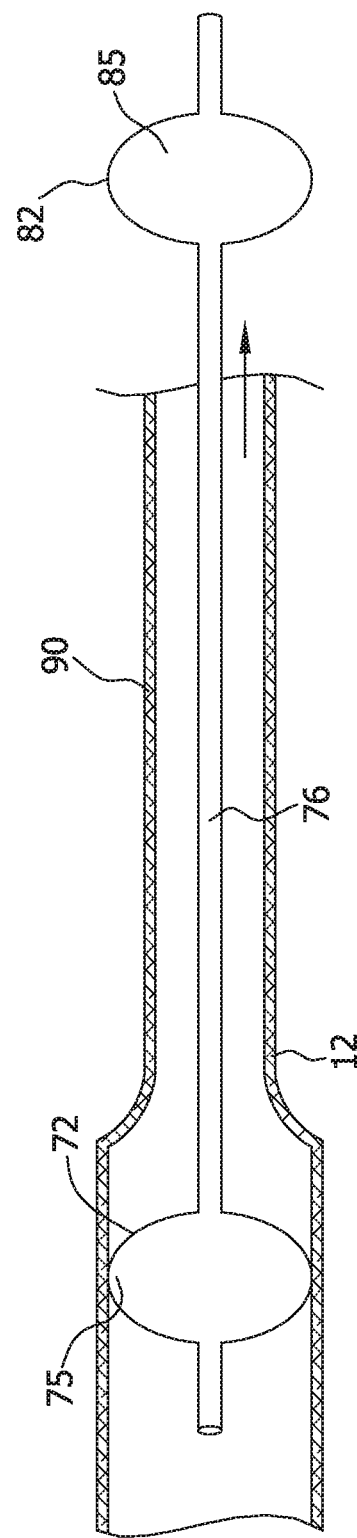
FIG. 12 is a schematic side view of the catheter shown in FIG. 11 positioned within a blood vessel having a region with a convergent cross-sectional area.
Figure 13:
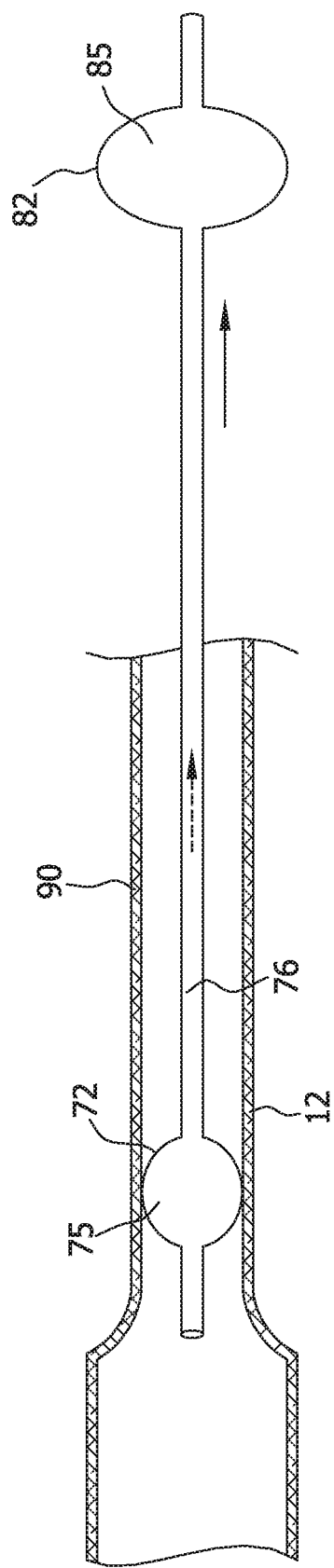
FIG. 13 is a schematic side view of the catheter shown in FIG. 11 positioned within the region with a convergent cross-sectional area.
Figure 14:
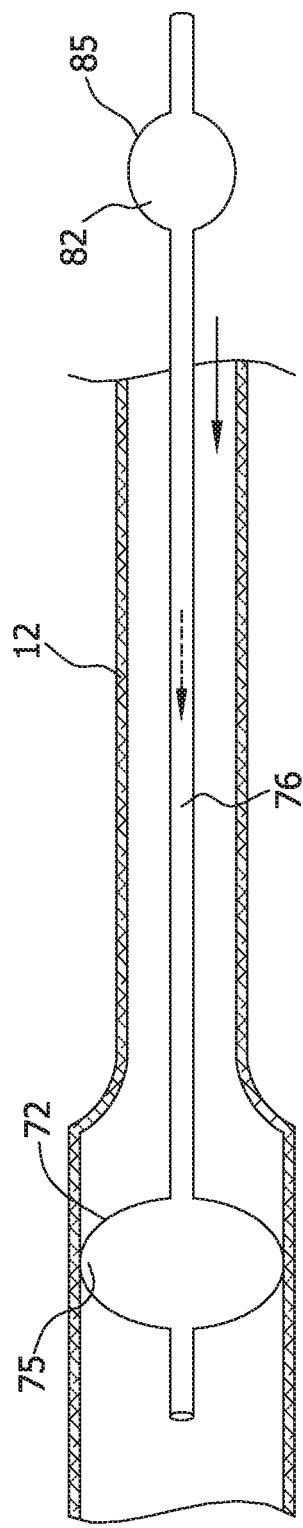
FIG. 14 is a schematic side view of the catheter shown in FIG. 11 positioned within a blood vessel having a region with a convergent cross-sectional area.

In the exemplary embodiment, an outer circumference of first expandable body 72 is adjustable to conform to the inner surface of blood vessel 12. Further, first expandable body 72 can be expanded to a specific or desired shape by inflating first balloon 75. In this embodiment, second expandable body 82 is configured to collapse in order to expand first expandable body 72. As second expandable body 82 is collapsed, fluid, such as a suitable gas, is transferred from within second expandable body 82 and/or passage 76 into first expandable body 72 to increase a volume of fluid contained within first expandable body 72 and correspondingly increase the outer circumference of first expandable body 72, as shown in FIG. 14 for example, to conform to the inner surface of blood vessel 12 without damaging the inner surface of blood vessel 12 or rupturing or tearing the blood vessel wall. Conversely, if the volume within first expandable body 72 is decreased, such as by translating catheter 70 through a region 90 of blood vessel 12 having a decreasing cross-section area, as shown in FIGS. 12 and 13, fluid from within first expandable body 72 is transferred into passage 76 and/or second expandable body 82, thus decreasing the volume of fluid contained within first expandable body 72 and increasing a volume of fluid contained within second expandable body 82.

Referring to FIGS. 1-14, one or more embodiments of a method for removing a thrombus from within a blood vessel are described herein. For example, a method for removing thrombus 14 from within blood vessel 12 using extraction device 20 includes introducing inner sheath 32 through passage 24 defined in outer sheath 22 positioned within blood vessel 12 proximate thrombus 14. Outer sheath 22 is extracted from within blood vessel 12 to expand inner sheath 32 along a length of inner sheath 32 to contact an inner surface of blood vessel 12. As outer sheath 22 is extracted from blood vessel 12, inner sheath 32 extends from distal end 28 of outer sheath 22 and expands to conform to the inner surface of blood vessel 12. In the exemplary embodiment, inner sheath 32 expands along substantially the entire length of inner sheath 32. In a particular embodiment, inner sheath 32 self-expands to match an inner circumference of blood vessel 12. As inner sheath 32 expands in a radial direction, inner sheath 32 contacts the inner surface of blood vessel 12.

With outer sheath 22 retracted from within blood vessel 12 and removed percutaneously through the incision, catheter 70 is introduced into inner sheath 32 and moved through inner sheath 32 to extend catheter 70 through thrombus 14. With at least distal end portion 78 of catheter 70 extended through thrombus 14, first expandable body 72 positioned at distal end portion 78 of catheter 70 is expanded to move first expandable body 72 radially outward toward the expanded configuration to conform to the inner surface of blood vessel 12. With an outer surface of first expandable body 72 contacting and conforming to the inner surface of blood vessel 12, catheter 70 and expanded first expandable body 72 are retracted into distal end 38 of inner sheath 32 to retain thrombus 14 within inner sheath 32. Thrombus 14 is then removed from within blood vessel 12.

In a particular embodiment, first expandable body 72 positioned at distal end portion 78 of catheter 70 includes first inflatable balloon 75 positioned at distal end portion 78 of catheter 70. Catheter 70 is then moved, with first inflatable balloon 75 inflated, into distal end 38 of inner sheath 32. With thrombus 14 retained with inner sheath 32, first inflatable balloon 75 may be partially deflated to facilitate translating catheter 70 through blood vessel 12 as desired.

In one embodiment, outer sheath 22 is introduced percutaneously into blood vessel 12 proximate thrombus 14. Inner sheath 32 is then inserted into outer sheath 22 and inner sheath 32 in a collapsed or partially collapsed configuration is moved through outer sheath 22 toward thrombus 14. Inner sheath 32 self-expands in a radial direction as inner sheath 32 moves relative to outer sheath 22 and exits distal end 28 of outer sheath 22.

The above-described extraction device can be introduced into a vessel, such as an occluded blood vessel, percutaneously for extracting emboli or thrombi from within the blood vessel. The minimally invasive percutaneous introduction reduces or minimizes trauma to the patient without the need for general anesthesia or hospitalization. In one embodiment, once the inner sheath has been positioned within the outer sheath and proximate the thrombus, the outer sheath can be removed from within the blood vessel to allow the inner sheath to expand in a radial direction substantially along an entire length of the inner sheath to facilitate removal of the thrombus from within the blood vessel. Further, the catheter as described herein includes a first expandable body, such as a first inflatable balloon, positioned distally with respect to the thrombus and a second expandable body, such as a second inflatable balloon, positioned external to the incision that cooperate to transfer fluid into or out of the first expandable body to increase or decrease, respectively, a volume of fluid contained within the first expandable body. This transfer of fluid allows the outer circumference of the first expandable body to be accurately adjusted to conform to the inner surface of the blood vessel without applying an undesired pressure against the blood vessel that may damage the inner surface of the blood vessel or tear or rupture the blood vessel wall.

Exemplary embodiments of a percutaneous thrombus extraction device and methods of utilizing the thrombus extraction device for removing emboli or thrombi from within a blood vessel are described above in detail. The extraction device is not limited to the specific embodiments described herein, but rather, components of the extraction device may be utilized independently and separately from other components described herein. Further, the described extraction device can also be defined in, or used in combination with, other devices and/or methods, and are not limited to practice with only the extraction device as described herein.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An extraction device for removing a thrombus from within a blood vessel, the extraction device comprising:
   a flexible outer sheath defining a first passage between an outer sheath proximal end and an outer sheath distal end;
   a first inner sheath extending out from the outer sheath distal end, the first inner sheath defining a second passage between a first inner sheath proximal end and a first inner sheath distal end; and
   a catheter movable within the second passage and for extending out of the first inner sheath distal end, the catheter comprising a tube comprising a plurality of apertures and a distal end having a second inner sheath expandable to contact an inner surface of the blood vessel to draw the thrombus into the second inner sheath to facilitate removing the thrombus from the blood vessel.

2. The extraction device of claim 1 wherein a portion of the first inner sheath comprises a mesh material and a portion of the second inner sheath comprises a mesh material.

3. The extraction device of claim 1 wherein the first inner sheath is constructed of a mesh material.

4. The extraction device of claim 1 wherein a portion of the first inner sheath is constructed of a mesh material.

5. The extraction device of claim 1 wherein a portion of the second inner sheath is constructed of a mesh material.

6. The extraction device of claim 1 further comprising a first radio opaque marker located at a first position on a circumferential edge of the distal end of the first inner sheath.

7. The extraction device of claim 6 further comprising a second radio opaque maker located at a second position on the circumferential edge of the distal end of the first inner sheath wherein the first position and the second position are located on a line defining a diameter of the first inner sheath.

8. The extraction device of claim 1 wherein the second inner sheath is constructed of a mesh material.

9. An extraction device for removing a thrombus from within a blood vessel, the extraction device comprising:
   a flexible outer sheath defining a first passage between an outer sheath proximal end and an outer sheath distal end;
   an expandable first inner sheath movable within the first passage, the first inner sheath defining a second passage between a first inner sheath proximal end and a first inner sheath distal end, the expandable first inner sheath extendable from the distal end of the outer sheath, the expandable first inner sheath movable between an expanded configuration and a collapsed configuration with a portion of the first inner sheath comprised of a mesh material, the mesh material further comprising a tube comprising a plurality of apertures to provide fluid communication between an inner lumen of the tube and the blood vessel; and
   a catheter movable within the second passage and for extending out of the first inner sheath distal end, the catheter comprising a distal end having a second inner sheath expandable to contact an inner surface of the blood vessel to draw the thrombus into the second inner sheath and the second passage of the first inner sheath to facilitate removing the thrombus from the blood vessel.

10. The extraction device of claim 9 further comprising a first radio opaque marker located at a first position on a circumferential edge of the distal end of the first inner sheath.

11. The extraction device of claim 10 further comprising a second radio opaque marker located at a second position on a circumferential edge of the distal end of the first inner sheath.

12. The extraction device of claim 9 wherein the second inner sheath comprises a mesh material.

13. The extraction device of claim 9 wherein the expandable first inner sheath in the expanded configuration is configured to retain the thrombus to facilitate removal of the thrombus within the blood vessel.

14. The extraction device of claim 9 wherein a portion of the second inner sheath is constructed of a mesh material.

15. The extraction device of claim 9 further comprising a first radio opaque marker located at a first position on a circumferential edge of the distal end of the first inner sheath and a second radio opaque maker located at a second position on the circumferential edge of the distal end of the first inner sheath opposing the first position.

16. The extraction device of claim 15 wherein the first position and the second position are located on a line defining a diameter of the first inner sheath.

17. An extraction device for removing a thrombus from within a blood vessel, the extraction device comprising:
   a flexible outer sheath defining a first passage between an outer sheath proximal end and an outer sheath distal end, the outer sheath distal end having an outer sheath distal end opening;
   a first inner sheath extending out of the distal end of the outer sheath, the first inner sheath defining a second passage between a first inner sheath proximal end and a first inner sheath distal end, and having a first inner sheath distal end opening; and
   a catheter movable within the second passage, the catheter comprising a distal end having a second inner sheath with a portion of the second inner sheath comprised of a mesh material, the catheter further comprising a tube comprising a plurality of apertures, the second inner sheath expandable to contact an inner surface of the blood vessel to draw the thrombus into the second inner sheath and the second passage of the first inner sheath to facilitate removing the thrombus from the blood vessel, and capable of extending out of the first inner sheath distal end opening.

18. The extraction device of claim 17 wherein the first inner sheath is constructed of a mesh material.

19. The extraction device of claim 17 wherein a portion of the first inner sheath is constructed of a mesh material.

20. The extraction device of claim 17 further comprising a first radio opaque marker located at a first position on a circumferential edge of the distal end of the first inner sheath.

* * * * *